US008404851B2

(12) United States Patent
Thuring et al.

(10) Patent No.: US 8,404,851 B2
(45) Date of Patent: Mar. 26, 2013

(54) 1,3,5-TRISUBSTITUTED TRIAZOLE DERIVATIVE

(75) Inventors: Johannes Wilhelmus John F. Thuring, Antwerpen (BE); Theodorus Dinklo, Beerse (BE); Anne Simone Josephine Lesage, Halle-Zoersel (BE)

(73) Assignee: Janssen Pharmaceutica NV, Beerse (BE)

( * ) Notice: Subject to any disclaimer, the term of this patent is extended or adjusted under 35 U.S.C. 154(b) by 166 days.

(21) Appl. No.: 12/738,725

(22) PCT Filed: Oct. 15, 2008

(86) PCT No.: PCT/EP2008/063844
§ 371 (c)(1),
(2), (4) Date: Apr. 19, 2010

(87) PCT Pub. No.: WO2009/050185
PCT Pub. Date: Apr. 23, 2009

(65) Prior Publication Data
US 2010/0240707 A1  Sep. 23, 2010

(30) Foreign Application Priority Data
Oct. 18, 2007  (EP) ..................... 07118822

(51) Int. Cl.
C07D 401/00 (2006.01)
A61K 31/44 (2006.01)
(52) U.S. Cl. ..................... 546/272.4; 514/338
(58) Field of Classification Search .......... None
See application file for complete search history.

(56) References Cited

U.S. PATENT DOCUMENTS

| 3,933,838 | A  | 1/1976  | Manghisi et al. |
| 6,187,797 | B1 | 2/2001  | Pruitt et al. |
| 6,569,874 | B1 | 5/2003  | Pruitt et al. |
| 8,143,419 | B2 | 3/2012  | Thuring et al. |
| 2004/0073029 | A1 | 4/2004 | Pruitt et al. |
| 2004/0254236 | A1 | 12/2004 | Dong et al. |
| 2005/0004134 | A1 | 1/2005 | Tsutsumi et al. |
| 2006/0063756 | A1 | 3/2006 | Salituro et al. |
| 2010/0216846 | A1 | 8/2010 | Thuring et al. |
| 2010/0324053 | A1 | 12/2010 | Macdonald et al. |
| 2011/0065683 | A1 | 3/2011 | Thuring et al. |
| 2011/0269748 | A1 | 11/2011 | Thuring et al. |
| 2012/0172354 | A1 | 7/2012 | Macdonald et al. |
| 2012/0238561 | A1 | 9/2012 | Macdonald et al. |

FOREIGN PATENT DOCUMENTS

| EP | 267986 A | 5/1988 |
| EP | 275312 A | 7/1988 |
| EP | 248523 B1 | 10/1991 |
| EP | 1205478 A | 5/2002 |
| EP | 1044970 | 1/2003 |
| EP | 1070708 A1 | 1/2004 |
| WO | WO 96/03392 A1 | 2/1996 |
| WO | WO 97/05131 A | 2/1997 |
| WO | WO 98/15543 A | 4/1998 |
| WO | WO 98/28282 A2 | 7/1998 |
| WO | WO 99/21555 A2 | 5/1999 |
| WO | WO 01/44207 A2 | 6/2001 |
| WO | WO 01/64674 A | 9/2001 |
| WO | WO 01/74793 A | 10/2001 |
| WO | WO 02/24200 A | 3/2002 |
| WO | WO 02/42298 A | 5/2002 |
| WO | WO 02/057240 | 7/2002 |
| WO | WO 03/015773 A | 2/2003 |
| WO | WO 03/062215 A | 7/2003 |
| WO | WO 03/094831 A3 | 11/2003 |
| WO | WO 2004/096225 A | 11/2004 |
| WO | WO 2004/110350 A | 12/2004 |
| WO | WO 2005/012263 A1 | 2/2005 |
| WO | WO 2005/051917 A1 | 6/2005 |
| WO | WO 2006/064375 A2 | 6/2005 |
| WO | WO 2005/070926 A | 8/2005 |
| WO | WO 2006/047256 | 5/2006 |
| WO | WO 2007/031440 A2 | 3/2007 |
| WO | WO 2007/118903 | 10/2007 |
| WO | WO 2007/118903 A1 | 10/2007 |
| WO | WO 2009/127678 A1 | 10/2009 |
| WO | WO 2012/113850 | 8/2012 |

OTHER PUBLICATIONS

Vippagunta, S. et al Advanced Drug Delivery Reviews, 2001, vol. 48, pp. 3-26.*
Silverman, R. "The Organic Chemistry of Drug Design and Drug Action," 2004, Elsevier, pp. 29-32.*
Chen et al., in Bioorganic & Medicinal Chemistry Letters 11 (2001) 3165-3168.
Makara G.M., et al. (Organic Letters (2002) vol. 4 (10); 1751-1754.
International Search Report for PCT/EP2008/063844 dated Dec. 30, 2008.

(Continued)

Primary Examiner — Janet Andres
Assistant Examiner — Heidi Reese
(74) Attorney, Agent, or Firm — Hal B. Woodrow

(57) ABSTRACT

The present invention relates to 2-[3-(2,2-Difluoro-benzo[1,3]dioxol-5-ylamino)-5-(2,6-dimethyl-pyridin-4-yl)-[1,2,4]triazol-1-yl]-N-ethyl-acetamide and analogues or pharmaceutically acceptable salts thereof, processes for preparing them, pharmaceutical compositions containing them and their use in therapy.

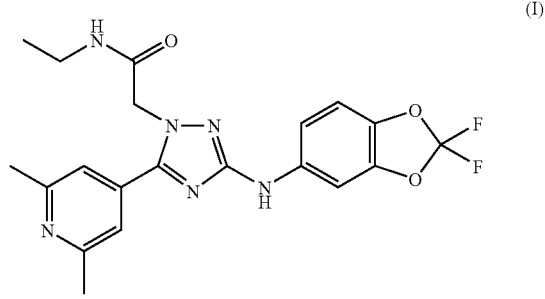

(I)

The invention particularly relates to a potent positive allosteric modulator of nicotinic acetylcholine receptors which have the capability of increasing the efficacy of nicotinic receptor agonists.

6 Claims, No Drawings

OTHER PUBLICATIONS

Dalack, Gregory W. et al., "Nicotine Dependence in Schizophrenia: Clinical Phenomena and Laboratory Findings", Am J Psychiatry, Nov. 1998, pp. 1490-1500, vol. 155:11.

Freedman, Robert et al., "Linkage of a neurophysiological deficit in schizophrenia to a chromosome 15 locus", Proc. Natl. Acad. Sci. USA, Jan 1997, pp. 587-592, V. 94.

Intelihealth, "Alzheimer's disease," online, accessed Jun. 30, 2008, http://www.intelihealth.com/IH/intlhlWSIHWOOO/8303/9117/195703.html?d=dmtHealthAZ.

Intelihealth, "Dementia," online, accessed Sep. 22, 2009, http://www.intelihealth.com/IH/ihtIHIWSIHWOOO/24479/11184.html.

Intelihealth, "Schizophrenia" online, accessed Oct. 4, 2011, http://www.intelihealth.com/IH/ihtIHIWSIHWOOO/8271 /8694/1 8801 O. html?d=dmtHealthAZ#prevent.

Nagamatsu, Tomohisa et al., "Syntheses of 3-Substituted 1-Methyl-6-phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).

Ridley, Diana L. et al., "Differential effects of chronic drug treatment on α3* and α7 nicotinic receptor binding sites, in hippocampal neurons and SH-SY5Y cells", British Journal of Pharmacology, (2001), pp. 1286-1295, vol. 133.

Stetter, Hermann et al., The Catalyzed Nucleophilic Addition of Aldehydes to Electrophilic Double Bonds*, Organic Reactions, (1991), pp. 407-496, vol. 40, Chapter 4.

U.S. Appl. No. 13/512,464, Macdonald et al.

Office Action mailed Aug. 12, 2011 in U.S. Appl. No. 12/063,689.

Office Action mailed Dec. 21, 2011 in U.S. Appl. No. 12/063,689.

Final Office Action mailed Apr. 5, 2012 in U.S. Appl. No. 12/063,689.

Notice of Allowance mailed Jul. 23, 2012 in U.S. Appl. No. 12/063,689.

Office Action mailed Oct. 13, 2011 in U.S. Appl. No. 12/738,763.

Office Action mailed Dec. 14, 2011 in U.S. Appl. No. 12/738,763.

Final Office Action mailed Apr. 19, 2012 in U.S. Appl. No. 12/738,763.

Notice of Allowance mailed Aug. 9, 2012 in U.S. Appl. No. 12/738,763.

Office Action mailed May 2, 2012 in U.S. Appl. No. 12/866,054.

Office Action mailed Aug. 10, 2012 in U.S. Appl. No. 12/866,054.

Office Action mailed Mar. 15, 2012 in U.S. Appl. No. 12/991,119.

Office Action mailed Jun. 22, 2012 in U.S. Appl. No. 12/991,119.

Banerjee, Carolin et al., "Cellular Expression of α7 Nicotinic Acetylcholine Receptor Protein in the emporal Cortex in Alzheimer's and Parkinson's Disease—A Stereological Approach", Neurobiology of Disease, (2000), pp. 666-672, vol. 7.

Bickford, Paula C. et al., "Restoration of sensory gating of auditory evoked response by nicotine in fimbria-fornix lesioned rats", Brain Research, (1995), pp. 235-240, vol. 705.

Brown, D.J. et al., "The Chemistry of heterocyclic compounds: Fused Pyrimidines", Book—The Chemistry of Heterocyclic compounds, (1971), pp. 261-304, Chapter IV.

Burghaus, Lothar et al., "Quantitative assessment of nicotinic acetylcholine receptor proteins in the cerebral cortex of Alzheimer patients", Molecular Brain Research, (2000), pp. 385-388, vol. 76.

Dalack, Gregory W. et al., "Nicotine Dependence in Schizophrenia: Clincal Phenomena and Laboratory Findings", Am J Psychiatry, Nov. 1998, pp. 1490-1500, vol. 155:11.

Dani, John A. et al., "Variations in desensitization of nicotinic acetylcholine receptors from hippocampus and midbrain dopamine areas", European Journal of Pharmacology, (2000), pp. 1-38, vol. 393.

Freedman, Robert et al., "Evidence in Postmortem Brain Tissue for Decreased Numbers of Hippocampal Nicotinic Receptors in Schizophrenia", Biol Psychiatry, (1995), pp. 22-33, vol. 38.

Freedman, Robert et al., "Linkage of Neurophysiological deficit in schizophrenia to a chromosome 15 locus", Proc. Natl. Acad. Sci. USA, Jan. 1997, pp. 587-592, V. 94.

Gol'din et. al.. Hcaplus Abstract 1974:437516, "Synthesis of triazolones and C-aminotriazoles by the thermal condensation of carbamidoamidrazones", 1974.

Grant, Morris, Guillory (in Brittain ed.), "Polymorphism, etc.," NY: Marcel Dekker, Inc., 1999, 1-2, 125-181, 183-226.

Griffith, Jay M. et al., "Nicotinic Receptor Desensitization and Sensory Gating Deficits in Schizophrenia", Biol Psychiatry, 1998, pp. 98-106, vol. 44.

Guan, Zhi-Zhong et al., "Decreased protein level of nicotinic receptor α7 subunit in the frontal cortex from schizophrenic brain", NeuroReport, Jun. 3, 1999, pp. 1779-1782, vol. 10 No. 8.

Hamill, O. P. et al., "Improved Patch-Clamp Techniques for High-Resolution Current Recording from Cells and Cell-Free Membrane Patches", Pflugers Arch, (1981) pp. 85-100, vol. 391.

Intelihealth, "Alzheimer's disease," online, accessed Jun. 30, 2008, http://www.intelihealth.com/IH/intlhIWSIHWOOO/8303/9117/195703.html?d=dmtHealthAZ.

Intelihealth, "Dementia," online, accessed Sep. 22, 2009, http://www.intelihealth.com/IH/ihtIHIWSIHWOOO/24479/11184.html.

Intelihealth, "Parkinson's disease," online, accessed Sep. 22, 2009, http://www.intelihealth.com/IH/ihtIH?d=dmtHealthAZ&c=201957.

Intelihealth, "Schizophrenia" online, accessed Oct. 4, 2011, http://www.intelihealth.com/IH/ihtIHIWSIHWOOO/8271 /8694/1 8801 O.html?d=dmtHealthAZ#prevent.

Leonard, Sherry et al., "Association of Promoter Variants in the α7 Nicotinic Acetylcholine Receptor Subunit Gene With an Inhibitory Deficit Found in Schizophrenia", Arch Gen Psychiatry, Dec. 2002, pp. 1085-1096, vol. 59.

Lin et. al., "Recent developments in neuronal nicotinic acetylcholine receptor modulators", 1998, 8 (8), pp. 991-1015.

Marutle, Amelia et al., "Laminar distribution of nicotinic receptor subtypes in cortical regions in schizophrenia", Journal of Chemical Neuroanatomy, (2001), pp. 115-126, vol. 22.

Muccioli, et al., "Latest Advances in Cannadinoid Receptor Antagonists and Inverse Agonists", Expert Opinion on Therapeutic Patents, vol. 16, No. 10, pp. 1405-1423, (2006).

Nagamatsu, Tomohisa et al., "General syntheses of -alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans., 2001, pp. 130-137.

Nagamatsu, Tomohisa et al., "Syntheses of 3-Substituted 1-Methyl-6- phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).

Ray, M.A. et al., "Neuronal nicotinic acetylcholine receptor subunits in autism: An immunohistochemical investigation in the thalamus", Neurobiology of Disease, (2005), pp. 366-377, vol. 19.

Ridley, Diana L. et al., "Differential effects of chronic drug treatment on α3* and α7 nicotinic receptor binding sites, in hippocampal neurons and SH-SY5Y cells", British Journal of Pharmacology, (2001), pp. 1286-1295, vol. 133.

Stetter, Hermann et al., The Catalyzed Nucleophilic Addition of Aldehydes to Electrophilic Double Bonds*, Organic Reactions, (1991), pp. 407-496, vol. 40, Chapter 4.

Virginio, Caterina et al., "Pharmacological properties of rat α7 nicotinic receptors expressed in native and recombinant cell systems", European Journal of Pharmacology, (2002), pp. 153-161, vol. 445.

West, Anthony R., Solid State Chemistry and its Applications, Wiley, New York, 1988, pp. 358 & 365.

Yu et al., "Physical characterization of, etc.," PSTT, vl. 1(3), 118-127 (1998).

* cited by examiner

US 8,404,851 B2

1,3,5-TRISUBSTITUTED TRIAZOLE DERIVATIVE

CROSS REFERENCE TO RELATED APPLICATIONS

This application is the national stage of PCT Application No. PCT/EP2008/063844, filed Oct. 15, 2008, which claims priority from European Patent Application No. 07118822.1, filed Oct. 18, 2007, the entire disclosures of which are hereby incorporated in their entirety.

The present invention relates to 2-[3-(2,2-difluoro-benzo[1,3]dioxol-5-ylamino)-5-(2,6-dimethyl-pyridin-4-yl)-[1,2,4]triazol-1-yl]-N-ethyl-acetamide and pharmaceutically acceptable salts thereof, processes for preparing them, pharmaceutical compositions containing them and their use in therapy. The invention relates to selective, potent positive allosteric modulators of α7 nicotinic acetylcholine receptors which have the capability of increasing the efficacy of nicotinic receptor agonists.

BACKGROUND PRIOR ART

EP 1044970 describes 3-alkylamino-1,2,4-triazoles as neuropeptide Y receptor ligands.

The paper by Makara G. M., et al. (Organic Letters (2002) Vol. 4 (10); 1751-1754) describes the solid-phase synthesis of 3-alkylamino-1,2,4-triazoles and exemplifies the unsuccessful synthesis of N-(4-methoxyphenyl)-1-methyl-5(4-methylphenyl)-1H-1,2,4-triazol-3-amine [CAS No: 433710-55-5] and is silent about potential therapeutic applications of this compound, in particular about its use as a positive allosteric modulator of the α7 nicotinic acetylcholine receptor.

Chen Chen et al., in Bioorganic & Medicinal Chemistry Letters 11 (2001) 3165-3168 describes the synthesis of 1-alkyl-3-amino-5-aryl-1H-[1,2,4]triazoles, in particular N-(2-methoxyphenyl)-1-methyl-5-(2,4-dichlorophenyl)-1H-1,2,4-triazol-3-amine, and their use as corticotropin-releasing factor-1 (CRF1) antagonists.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit or memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and particularly at the α7-nicotinic receptor, desensitization limits the duration of action of an applied agonist.

DESCRIPTION OF THE INVENTION

We have surprisingly found that 2-[3-(2,2-Difluoro-benzo[1,3]dioxol-5-ylamino)-5-(2,6-dimethyl-pyridin-4-yl)-[1,2,4]triazol-1-yl]-N-ethyl-acetamide can increase the efficacy of agonists at nicotinic acetylcholine receptors. Compounds having this type of action are referred to as "positive allosteric modulators" and are likely useful for treatment of conditions associated with reductions in nicotinic transmission. In a therapeutic setting such compound could restore normal interneuronal communication without affecting the temporal profile of activation. In addition, positive allosteric modulators are not expected to produce long-term inactivation of receptors as may occur after repeated or prolonged application of agonists.

The positive nAChR modulator of the present invention is useful for treatment or prophylaxis of psychotic disorders, intellectual impairment disorders or diseases, inflammatory diseases or conditions in which modulation of the α7 nicotinic receptor is beneficial.

The present invention concerns 2-[3-(2,2-difluoro-benzo[1,3]dioxol-5-ylamino)-5-(2,6-dimethyl-pyridin-4-yl)-[1,2,4]triazol-1-yl]-N-ethyl-acetamide having positive allosteric modulator properties, increasing the efficacy of agonists at the α7 nicotinic receptor. The invention further relates to methods for preparation and pharmaceutical compositions comprising them. The invention also relates to the use of this derivative for the manufacture of a medicament for the treatment or prophylaxis of psychotic disorders, intellectual impairment disorders or diseases or conditions in which modulation of the α7 nicotinic receptor is beneficial.

The compound and the salts thereof of the present invention differs structurally from the prior art compounds and pharmacologically by its enhanced activity as a positive allosteric modulator of the α7 nicotinic acetylcholine receptor, by its enhanced aqueous solubility and by its improved in vitro cardiovascular safety parameters, in particular reduced affinity to the hERG potassium channel.

The present invention relates to the compound (I)

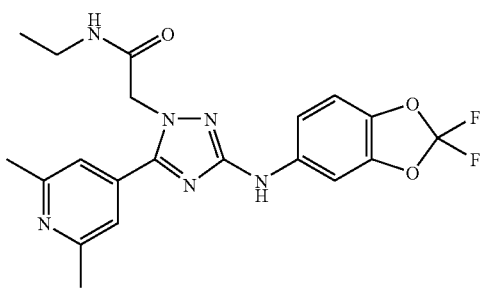

or a pharmaceutically acceptable salt or a hydrate or a solvate thereof.

For therapeutic use, salts of the compound according to formula (I) are those wherein the counterion is pharmaceutically acceptable. However, salts which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid addition salt forms which the compound (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The term hydrate and solvate refer to hydrates and alcoholates which the compounds according to formula (I) as well as the salts thereof, may form.

The compound according to formula (I) may also exist in tautomeric forms. Such forms although not explicitly indicated in the above formula are intended to be included within the scope of the present invention.

Preparation of the Compounds

A compound according to the invention can generally be prepared by a succession of steps, each of which is known to the skilled person. In particular, the compound in this patent application can be prepared according to the following preparation methods (Schemes 1 to 5).

Scheme 1

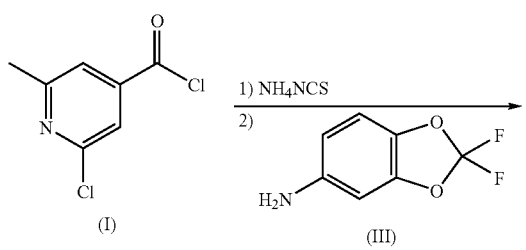

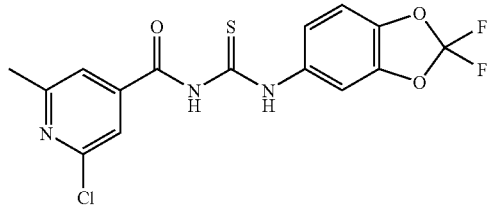

The acyl thiourea (II) is obtained in 2 stages. In a first stage, the acyl chloride (I) is reacted with a monovalent cation thiocyanate, such as for example ammonium thiocyanate to yield the corresponding acyl isothiocyanate. This reaction can be performed using acetone as a solvent and at a temperature between 0° C. and 70° C., preferably at room temperature.

In a second stage that can advantageously be performed in the same reaction medium, without isolating the intermediate acyl isothiocyanate, the aniline (III) is added to yield the N-acyl thiourea of the formula (II). This reaction is usually performed at a temperature between 0° C. and 70° C., preferably at room temperature (Scheme 1).

Scheme 2

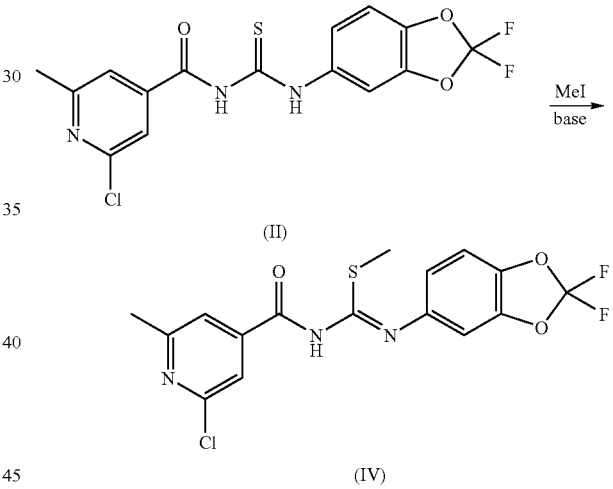

In a next step, S-methylation of the N-acyl thiourea (II) provides the N-acyl carbomimidothioic acid, methyl ester derivative of formula (IV). This transformation requires the presence of a base, preferably a strong inorganic base, such as NaH or potassium carbonate, and is performed in an aprotic solvent such as for example DMF, THF and the like, at a temperature ranging from −70° C. to room temperature, preferably 0° C. (Scheme 2).

Scheme 3

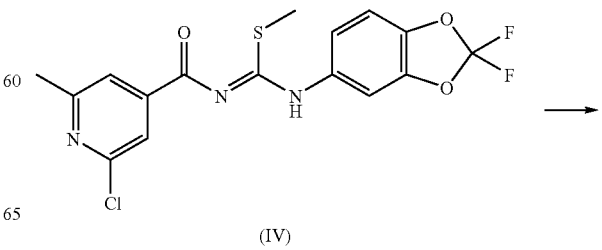

(V)

The N-acyl carbomimidothioic acid, methyl ester derivative of formula (IV) can be transformed into the 1,2,4-triazole of formula (V) using 2-hydrazinylacetic acid ethyl ester, hydrochloride salt. This transformation is typically performed in a protic solvent, such as methanol or a higher alcohol and requires a temperature between room temperature and 150° C. In a particular embodiment, the higher alcohol is tertiary butyl alcohol and the reaction temperature is between 70° and 120° C., most preferably 100° C. The addition of a stoichiometric amount of a base is preferred. Said base can be an inorganic base, such as potassium acetate or potassium carbonate, more preferably however, said base is a tertiary amine, such as diisopropyl ethyl amine or the like (Scheme 3).

Scheme 4

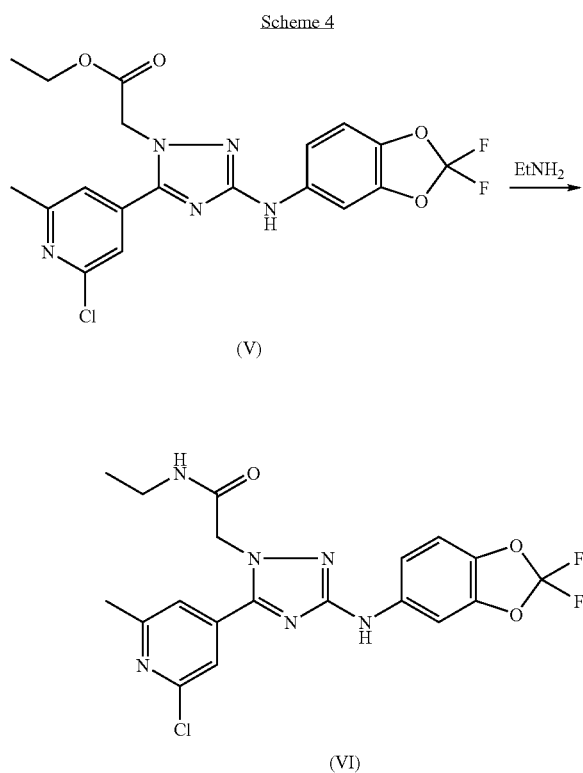

(V)

(VI)

The [1,2,4]triazol-1-yl]-acetic acid ethyl ester of the formula (V) is converted into the corresponding [1,2,4]triazol-1-yl]-N-ethyl-acetamide (VI), by treatment with an excess amount of ethyl amine in a protic solvent at a temperature between 0° and 80° C., preferably room temperature (Scheme 4).

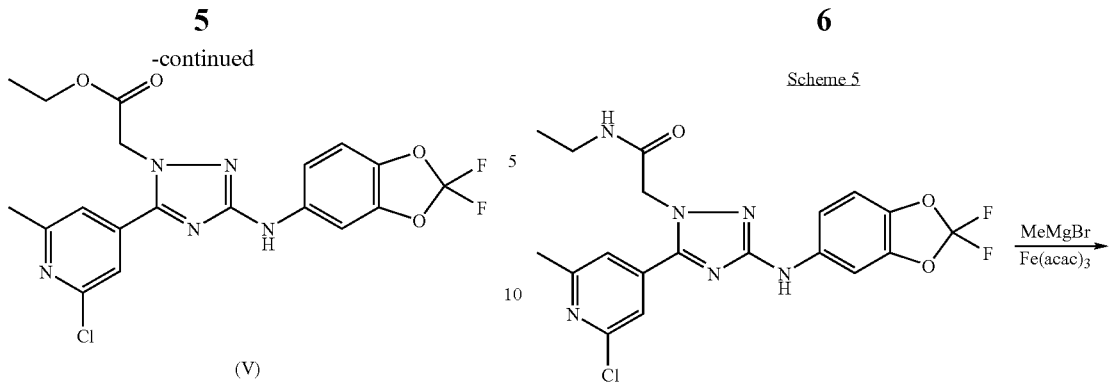

The final dimethyl-substituted pyrido triazole of the formula (I), can be prepared by treatment of the 2-chloro pyridyl precursor (VI) with excess (3-15 equiv.) Grignard reagent MeMgBr in the presence of a catalytic amount of Iron(III) acetylacetonate in a solvent system consisting of 75% to 85% THF and 15% to 25% NMP by volume. Said transformation can be performed in a temperature range between 0° C. and 50° C., most preferably between 0° C. and 25° C. (Scheme 5).

Pharmacology

The compound of the present invention was found to be a positive allosteric modulator of the α7 nicotinic receptor. The α7 nicotinic receptor (α7 nAChR) belongs to the superfamily of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the α7 locus on 15q13-14 and polymorphisms in core promoter region of the α7 gene.

Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein the PAM-induced increase in α7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 1-4, based on qualitative kinetic properties, as determined by whole-cell voltage-clamp recordings. This classification is based on the effect of an α7 PAM compound, as described hereinbefore, on the signal elicited by an agonist application. In particular, said agonist is choline at a concentration of 1 mM. In a preferred experimental setting, said α7 PAM compound and choline are simultaneously applied to the cell, as described hereinafter. Desensitization as described hereinafter is the closure of the receptor upon activation during the application of the agonist in whole-cell voltage-clamp electrophysiology measurements seen as the reduction of the outward current after initial activation by the agonist.

The definition of the PAM types 1-4 is described hereinafter:

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 μM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include, but are not limited to:

1,4-Diazabicyclo[3.2.2]nonane-4-carboxylic acid, 4-bromophenyl ester, monohydrochloride (SSR180711A);

(−)-spiro[1-azabicyclo[2.2.2.]octane-3,5'-oxazolidine]-2'-one;

3-[(2,4-Dimethoxy)Benzylidene]-Anabaseine Dihydrochloride (GTS-21);

[N-[(3R)-1-Azabicyclo[2.2.2]oct-3-yl]-4-chlorobenzamide Hydrochloride]PNU-282987).

The compound of the present invention is useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

The compound(s) may also find therapeutical use as (an) anti-inflammatory medicine(s) because the nicotinic acetylcholine receptor α7 subunit is essential for inhibiting cytokine synthesis by the cholinergic inflammatory pathway. Examples of indications which may be treated by the compound(s) are endotoxaemia, endotoxic shock, sepsis, rheumatoid arthritis, asthma, multiple sclerosis, inflammatory bowel disease, inflammatory bile disease, Crohn's disease, pancreatitis, heart failure, and allograft rejection.

In view of the above described pharmacological properties, the compound and its pharmaceutically acceptable addition salts may be used as a medicine. In particular, the present compound can be used for the manufacture of a medicament for treatment or prophylaxis of psychotic disorders, intellectual impairment disorders or diseases or conditions in which modulation of the α7 nicotinic receptor is beneficial.

In view of the utility of the compound, there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, a pharmaceutically acceptable addition salt, a solvate, or a hydrate thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 μM, and more usually 5 nM to 50 μM. To obtain these treatment concentrations, a patient in need of treatment likely will be administered between 0.005 mg/kg to 10 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional α7 nicotinic receptor agonists, such as for example 1,4-Diazabicyclo[3.2.2] nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy) Benzylidene]-Anabaseine Dihydrochloride (GTS-21); or [N-[(3R)-1-Azabicyclo[2.2.2]oct-3-yl]-4-chlorobenzamide Hydrochloride] PNU-282987). Thus, the present invention also relates to the combination of a compound according to formula (I) and a α7 nicotinic receptor agonist. Said combination may be used as a medicine. The present invention also relates to a product comprising (a) a compound according to formula (I), and (b) an α7 nicotinic receptor agonist, as a combined preparation for simultaneous, separate or sequential use in the treatment of diseases wherein modulation of the α7 nicotinic receptor is beneficial. The different drugs may be combined in a single preparation together with pharmaceutically acceptable carriers.

Experimental Part

Several methods for preparing the compounds of this invention are illustrated in the following Examples. Unless otherwise noted, all starting materials were obtained from commercial suppliers and used without further purification.

Hereinafter and hereinbefore, "DMF" means N,N-dimethylformamide; "NMP" means 1-methyl-2-pyrrolidinone; "THF" means tetrahydrofuran and "DIPE" means diisopropylether.

For LCMS-characterization of the intermediates and the compound of the present invention, the following methods were used.

General Procedure

The HPLC measurement was performed using an Alliance HT 2790 (Waters) system comprising a quaternary pump with degasser, an autosampler, a column oven (set at 60° C. for LCMS procedure 1 and at 40° C. for LCMS procedure 2), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS Procedure 1

In addition to the general procedure: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS Procedure 2 (Only Used for the Intermediates)

In addition to the general procedure: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 µl was used. Cone voltage was 10 V for positive ionization mode and 20 V for negative ionization mode.

Melting Point

The melting point (m.p.) was determined with a DSC823e (Mettler-Toledo). Melting points were measured with a temperature gradient of 30° C./minute. Maximum temperature was 400° C. Values are obtained with experimental uncertainties that are commonly associated with this analytical method.

A. Preparation of the Intermediates

Description 1

1-(2-Chloro-6-methyl-pyridine-4-carbonyl)-3-(2,2-difluoro-benzo[1,3]dioxol-5-yl)thiourea (D1)

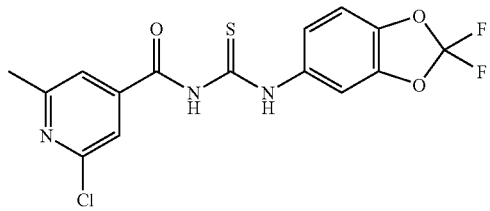 [SMILES: Cc1cc(C(=O)NC(=S)Nc2ccc3c(c2)OC(F)(F)O3)cc(Cl)n1]

Thiocyanic acid, ammonium salt (1:1) (9.35 g; 0.1230 mol) was stirred in 2-propanone (300 ml) at room temperature. 2-Chloro-6-methyl-4-pyridinecarbonylchloride (22.2 g; 0.1170 mol) was then added and the reaction mixture was stirred for 2 hours at room temperature. 2,2-Difluoro-1,3-benzodioxol-5-amine (19.2 g; 0.1110 mol) in some 2-propane was added and the reaction mixture was stirred for 1 hour at room temperature. The reaction mixture was then poured onto ice and the residue was filtered off and dried. Yield: 38.1 g of intermediate D1.

LCMS Retention time: 1.03; [M−H]⁻ peak: 384; LCMS procedure 2

Description 2

2-Chloro-N-[(2,2-difluoro-benzo[1,3]dioxol-5-ylamino)-methylsulfanyl-methyl]-6-methyl-isonicotinamide (D2)

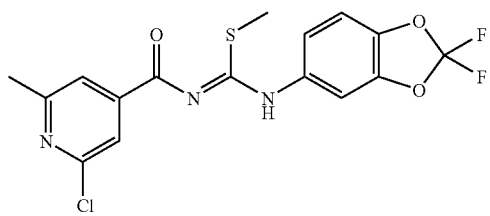 [SMILES: CS/C(=N\C(=O)c1cc(C)nc(Cl)c1)Nc1ccc2c(c1)OC(F)(F)O2]

NaH, 60% (2.2 g; 0.0550 mol) was stirred in THF (170 ml) on an ice bath under N$_2$. Intermediate D1 (19.3 g; 0.500 mol) was then added and stirred for 1 hour at 0° C. CH$_3$I (7.8 g; 0.0550 mol) was then added and the reaction mixture was allowed to warm to room temperature overnight. Water was added and the THF was evaporated in vacuo. The precipitate was filtered off, washed with water and dried. Yield: 22.86 g of intermediate D2.

LCMS Retention time: 1.15; [M−H]$^-$ peak: 398; LCMS procedure 2

Description 3

[5-(2-Chloro-6-methyl-pyridin-4-yl)-3-(2,2-difluoro-benzo[1,3]dioxol-5-ylamino)-[1,2,4]triazol-1-yl] acetic acid ethyl ester (D3)

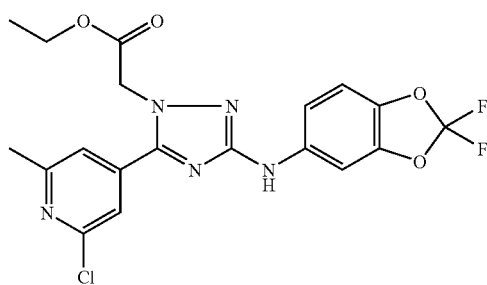 [SMILES: CCOC(=O)Cn1nc(Nc2ccc3c(c2)OC(F)(F)O3)nc1-c1cc(C)nc(Cl)c1]

Intermediate D2 (13.6 g; 0.0340 mol), 2-hydrazinylacetic acid ethyl ester, hydrochloride (1:1) (10.5 g; 0.0680 mol), N-ethyl-N-(1-methylethyl)-2-propanamine (13.2 g; 0.1020 mol) and t-BuOH (400 ml) were refluxed for 2 hours. The reaction mixture was then evaporated. Water was added and the product was extracted with CH$_2$Cl$_2$. The organic layer was dried on MgSO$_4$, filtered and evaporated in vacuo. The residue was then heated to 60° C. in ethanol/HCl for 1 hour. The reaction mixture was partly evaporated and, the precipitate was filtered off and dried. Yield: 4.57 g of intermediate D3.

LCMS Retention time: 1.03; [M−H]$^-$ peak: 450; LCMS procedure 2

Description 4

2-[5-(2-Chloro-6-methyl-pyridin-4-yl)-3-(2,2-difluoro-benzo[1,3]dioxol-5-ylamino)-[1,2,4]triazol-1-yl]-N-ethyl-acetamide (D4)

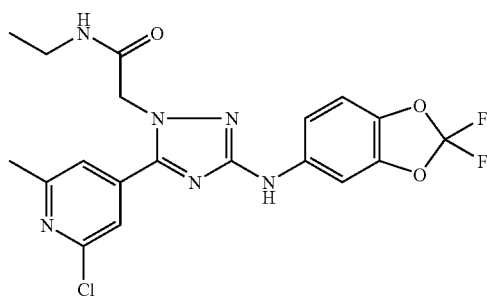 [SMILES: CCNC(=O)Cn1nc(Nc2ccc3c(c2)OC(F)(F)O3)nc1-c1cc(C)nc(Cl)c1]

Intermediate D3 (1 g; 0.0022 mol) and ethylamine in CH$_3$OH (40 ml; 2 M) were stirred at room temperature overnight. The product crystallized from the reaction mixture. The crystals were filtered off and dried. Yield: 700 mg of intermediate D4.

LCMS Retention time: 0.95; [M−H]$^-$ peak: 449; LCMS procedure 2

B. Preparation of the Final Compound

2-[3-(2,2-Difluoro-benzo[1,3]dioxol-5-ylamino)-5-(2,6-dimethyl-pyridin-4-yl)-[1,2,4]-triazol-1-yl]-N-ethyl-acetamide (E1)

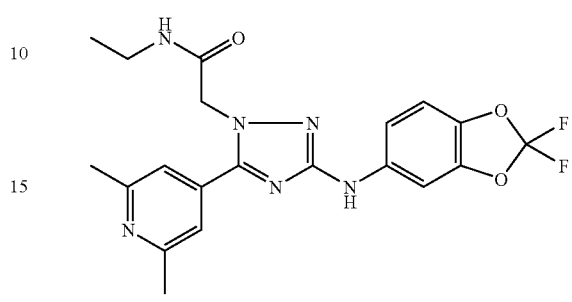

Intermediate D4 (0.70 g; 0.0016 mol), Iron(III) acetylacetonate (0.067 g; 0.0002 mol), THF (20 ml) and 1-methyl-2-pyrrolidinone (5 ml) were stirred at 0° C. under N$_2$. Excess CH$_3$MgBr in diethyl ether (2 M) was added and the mixture was brought to room temperature. The reaction mixture was then decomposed with CH$_3$OH and evaporated in vacuo. Water and CH$_2$Cl$_2$ were added and the mixture was filtered over dicalite. The filtrate was evaporated and water and DIPE were added. The precipitate was filtered off, dissolved in CH$_2$Cl$_2$, dried over MgSO$_4$, filtered and evaporated in vacuo. The residue was stirred in water, the precipitate was filtered off and dried. Yield: 400 mg of compound E1.

melting point: 242.28° C.

LCMS Retention time: 5.12; [M+H]$^+$peak: 431; LCMS procedure 1

$^1$H NMR (Bruker DPX 360 MHz, DMSO-d$_6$) δ ppm 9.62 (s), 8.37 (t, J=5.4 Hz), 7.67 (d, J=2.1 Hz), 7.38 (s), 7.29 (d, J=8.8 Hz), 7.22 (dd, J=8.8, 2.2 Hz), 4.84 (s), 3.13 (qd, J=7.2, 5.5 Hz), 2.50 (s), 1.03 (t, J=7.2 Hz)

C. Pharmacological Examples

Example C.1 b

Ca$^{2+}$ Flux Imaging (FDSS)

Materials
a) Assay Buffer
    Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium).
b) Calcium-Sensitive Dye—Fluo-4AM
    Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 μM.
c) 384-Well Plates
    Black 384 well plate black/clear plates, PDL pre-coated (Corning, Incorporated, USA)
d) Calcium Flux Measurement
    A Functional drug screening system (FDSS, Hamamatsu) was used to measure intracellular free-calcium flux signals.

Method

Monolayers of hα7-wt nAChR-expressing GH4C1 cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.

PAM activity was detected in real time by applying the compound to be tested to the loaded cells along with a α7 nicotinic receptor agonist during constant monitoring of the cellular calcium mobilization by fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a sub-maximal concentration of 100 µM. In a further setting of the present invention the compounds to be tested were applied prior to the α7 nicotinic receptor agonist, in a particular embodiment up to 10 minutes prior to the agonist.

A control response to choline was calculated on each plate from the difference in peak in fluorescence in wells receiving either choline or assay buffer alone. The compound of the present invention was tested at a concentration range from 0.01 µM to 30 µM. Compounds were considered to have an interesting activity when they potentiated the choline signal at least with 250% when tested at a concentration of 30 µM (the efficacy of 100 µM choline was defined as 100% in the absence of a PAM).

$EC_{50}$ values (potency), maximal effect (% efficacy), and Hill slopes were estimated by fitting the sigmoidal equation to the data using GraphPad Prism (GraphPad Software, Inc., San Diego, Calif.). An $EC_{50}$ (or $pEC_{50}$) was determined as a concentration relating to half the maximal effect, when a clear sigmoidal curve with top plateau was obtained.

The compound of the present invention also has a potentiating effect on the response to choline when measured by whole-cell voltage clamp electrophysiology in GH4C1 cells stably over-expressing the human wild-type α7 receptor, as described hereinafter.

Example C.2

Whole-Cell Voltage-Clamp Recording

Whole-cell voltage-clamp recording from mammalian cells has provided a powerful means of assessing the function of membrane proteins thought to be subunits of ligand-gated ion channels. Activation of such proteins by endogenous or exogenous ligands causes opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of an agonist it is important that an application system is used which is capable of very rapid switching of solutions (<100 ms) to prevent partial or full desensitization of receptor responses coincident with the time of agonist application. Consequently, a second convenient technique to assess the enhancement of nicotinic efficacy is whole-cell voltage-clamp recording from hα7-wt nAChR-expressing GH4C1 cells coupled with a rapid-application system.

Materials a) Assay Buffers

The external recording solution consisted of 152 mM NaCl, 5 mM KCl, 1 mM $MgCl_2$, 1 mM Calcium, 10 mM HEPES; pH 7.3. The internal recording solution consisted of 140 mM CsCl, 10 mM HEPES, 10 mM EGTA, 1 mM $MgCl_2$, pH 7.3.

b) Patch-clamp recording was carried out using a Patch-clamp amplifier (Multiclamp 700A, Axon Instruments, CA, USA). The membrane potential of hα7-wt nAChR-expressing GH4C1 cells was voltage-clamped in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1GΩ and series resistance <15 MΩ with at least 60% series resistance compensation. Membrane potential was clamped at −70 mV.

c) Agonists

ACh, choline, were purchased from Sigma-Aldrich NV, Belgium.

d) Compound Application

A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (0.75 µl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by the compound of the invention indicates that it is expected to have useful therapeutic activity.

TABLE 1

Potency ($pEC_{50}$) and % efficacy for compound E1.

| Comp. Nr. | $pEC_{50}$ | % efficacy | PAM_type |
|---|---|---|---|
| E1 | 6.51 | 1920 | 2 |

A type 2 compound reduces the rate and extent of desensitization.

The invention claimed is:

1. A compound of formula (I)

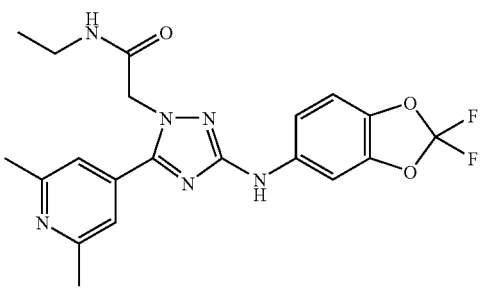 [SMILES: CCNC(=O)Cn1nc(Nc2ccc3c(c2)OC(F)(F)O3)nc1-c1cc(C)nc(C)c1]

or a pharmaceutically acceptable salt thereof.

2. A method for the treatment of schizophrenia or Alzheimer's disease, comprising administering a therapeutically effective amount of a compound according to claim 1.

3. A pharmaceutical composition comprising a pharmaceutically acceptable carrier and as active ingredient a therapeutically effective amount of a compound as claimed in claim 1.

4. A process of preparing a composition as claimed in claim 3, wherein a pharmaceutically acceptable carrier is intimately mixed with a therapeutically effective amount of a compound as claimed in claim 1.

5. A product comprising
   (a) a compound as claimed in claim 1, and
   (b) an α7 nicotinic receptor agonist,
as a combined preparation for simultaneous, separate, or sequential use in treating schizophrenia or Alzheimer's disease.

6. A process of preparing a compound as claimed in claim 1 comprising the step of reacting an intermediate of formula (VI) with an excess of

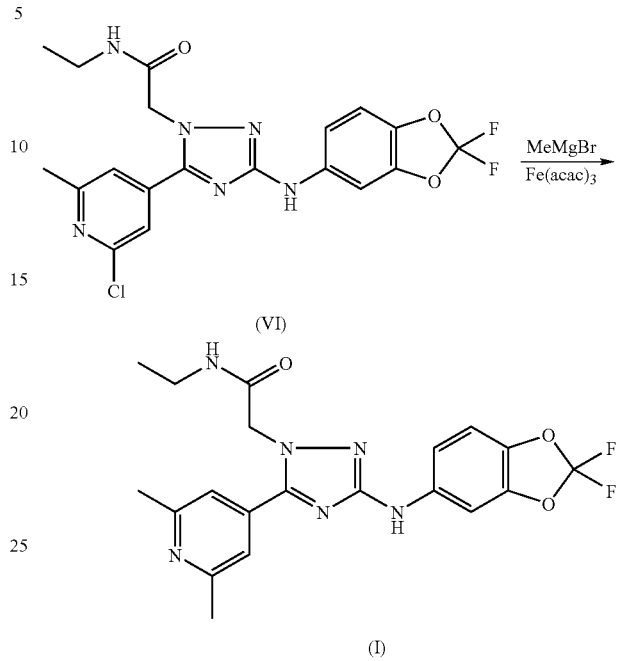

Grignard reagent MeMgBr in the presence of a catalytical amount of Iron(III)acetylacetonate in a solvent system consisting of 75% to 85% THF and 15% to 25% NMP by volume in a temperature range from 0 ° C. to 50 ° C.

* * * * *